US010368839B2

(12) United States Patent
Park

(10) Patent No.: US 10,368,839 B2
(45) Date of Patent: Aug. 6, 2019

(54) UNIT ULTRASONIC WAVE PROBE, ULTRASONIC WAVE PROBE MODULE HAVING SAME, AND ULTRASONIC WAVE PROBE DEVICE HAVING SAME

(71) Applicant: Humanscan Co., Ltd., Ansan-si, Gyeonggi-do (KR)

(72) Inventor: Wonseop Park, Seoul (KR)

(73) Assignee: HUMANSCAN CO., LTD., Ansan-si, Gyeonggi-do (KR)

(*) Notice: Subject to any disclaimer, the term of this patent is extended or adjusted under 35 U.S.C. 154(b) by 720 days.

(21) Appl. No.: 14/784,921

(22) PCT Filed: Apr. 2, 2014

(86) PCT No.: PCT/KR2014/002832
§ 371 (c)(1),
(2) Date: Oct. 15, 2015

(87) PCT Pub. No.: WO2014/181966
PCT Pub. Date: Nov. 13, 2014

(65) Prior Publication Data
US 2016/0058416 A1 Mar. 3, 2016

(30) Foreign Application Priority Data
May 9, 2013 (KR) ........................ 10-2013-0052445

(51) Int. Cl.
*A61B 8/00* (2006.01)
*A61B 8/08* (2006.01)
(Continued)

(52) U.S. Cl.
CPC .......... *A61B 8/4494* (2013.01); *A61B 8/0866* (2013.01); *A61B 8/4477* (2013.01);
(Continued)

(58) Field of Classification Search
CPC ................................ A61B 8/12; A61B 8/4281
See application file for complete search history.

(56) References Cited

U.S. PATENT DOCUMENTS

2003/0107303 A1 6/2003 Mohr, III et al.
2006/0186765 A1* 8/2006 Hashimoto ............ A61B 8/546 310/334

FOREIGN PATENT DOCUMENTS

JP 08173416 A 7/1996
JP 2008302044 A 12/2008
(Continued)

OTHER PUBLICATIONS

International Search Report for PCT/KR2014/002832 dated Jul. 1, 2014.
(Continued)

*Primary Examiner* — Hien N Nguyen
(74) *Attorney, Agent, or Firm* — Hauptman Ham, LLP

(57) ABSTRACT

The present invention relates to a unit ultrasonic wave probe, an ultrasonic wave probe module, and an ultrasonic wave probe device. The unit ultrasonic probe according to the present invention includes: a rear block part; a flexible substrate part arranged on the top of the rear block part; and a piezoelectric wafer arranged on the top of and electrically connected with the flexible substrate part, the wafer being formed to have a smaller size than the rear block part, so that even if increasing the number of piezoelectric wafers transversely, the number of channels is increased by depositing the unit ultrasonic wave probe including the piezoelectric wafer, thus preventing the cost from geometrically increasing because of the structure of the flexible substrate becoming complex.

10 Claims, 15 Drawing Sheets

(51) Int. Cl.
*B06B 1/06* (2006.01)
*G01N 29/22* (2006.01)
*G01N 29/24* (2006.01)

(52) U.S. Cl.
CPC ........... *B06B 1/064* (2013.01); *G01N 29/226* (2013.01); *G01N 29/2437* (2013.01); *G01N 2291/02475* (2013.01); *G01N 2291/106* (2013.01)

(56) References Cited

FOREIGN PATENT DOCUMENTS

| | | | |
|---|---|---|---|
| JP | 2011254295 | A | 12/2011 |
| JP | 2013042552 | A | 2/2013 |
| KR | 100917727 | B1 | 9/2009 |
| KR | 1020100091466 | A | 8/2010 |
| KR | 1020110088384 | A | 8/2011 |

OTHER PUBLICATIONS

Korean Notice of Allowance for application No. 10-2013-0052445 dated Jan. 27, 2015.

* cited by examiner 301
301a
301b
31
32
33
34
35
36
37
38
101
102
103
104
105
106
107
108

302
38
37
36
35
31
32
33
34
301a
301b
101
102
103
104
105
106
107
108

303
301a
301b
31
32
33
34
101
102
103
104
11
12
13
14
21
22
23
24

UNIT ULTRASONIC WAVE PROBE, ULTRASONIC WAVE PROBE MODULE HAVING SAME, AND ULTRASONIC WAVE PROBE DEVICE HAVING SAME

CROSS REFERENCE TO RELATED APPLICATION

This application claims the priority of Korean Patent Application No. 10-2013-0052445 filed on May 9, 2013 in the Korean Patent and Trademark Office. Further, this application is the National Phase application of International Application No. PCT/KR2014/002832 filed on Apr. 2, 2014, which is incorporated herein by reference in its entirety.

TECHNICAL FIELD

The present invention relates to a unit ultrasonic probe, an ultrasonic probe module having the same, and an ultrasonic probe device having the same, and more particularly, to a unit ultrasonic probe capable of easily increasing the number of piezoelectric wafers capable of transversally generating an ultrasonic wave and of implementing the same with low cost, an ultrasonic probe module having the same, and an ultrasonic probe device having the same.

BACKGROUND ART

Ultrasonic examinations are used to examine abnormal tissues using ultrasonic waves, identify the presence of the abnormal tissues using images generated through signals which are reflected ultrasonic waves radiated to diseased areas. The ultrasonic examinations are mainly used for examining lesion tissues such as tumors or in prenatal diagnosis.

Ultrasound is defined as sounds having frequencies greater than or equal to those of sounds which a human can hear, and normally, the ultrasound is in the frequency range of 20,000 Hz to 30 MHz. In this frequency range, diagnostic ultrasonic waves which are used for examining a human body are normally in the frequency range of 1 MHz to 20 MHz.

An ultrasonic imaging device may be a device to perform an ultrasonic examination, and be mainly divided into three parts, that is, an ultrasonic probe, a signal processor, and a display. The ultrasonic probe converts electrical and ultrasonic signals, the signal processor processes the received signals or the signals to be transmitted, and the display generates images using the signals received from the ultrasonic probe and the signal processor. Particularly, the ultrasonic probe is an important part that determines quality of the ultrasonic image.

In general, the ultrasonic probe includes a piezoelectric wafer, a rear block part, a flexible substrate part, and an acoustic lens, and the ultrasonic probe is becoming gradually miniaturized.

Accordingly, as the ultrasonic probe is miniaturized, the number of transversal channels is increased to improve a vibration characteristic and focusing in the ultrasonic probe, and a structure of a flexible substrate part is complicated. Accordingly, there are problems in that the manufacturing thereof is not easy and the manufacturing cost increases exponentially.

DISCLOSURE

Technical Problem

The present invention is directed to providing a unit ultrasonic probe, in which a structure of a flexible substrate part is simplified and not complicated even though the number of unit probes including a transversal piezoelectric wafer increases, which is easy to manufacture, and which prevents the cost from increasing exponentially, an ultrasonic probe module having the same, and an ultrasonic probe device having the same.

Technical Solution

One aspect of the present invention provides a unit ultrasonic probe including: a rear block part; a flexible substrate part disposed on an upper surface of the rear block part; and a piezoelectric wafer which is disposed on an upper surface of the flexible substrate part, is in electrical connection with the flexible substrate part, is formed smaller than the rear block part, and generates an ultrasonic wave.

The rear block part of the unit ultrasonic probe may have a first width and a first height, and the flexible substrate part may have the first height and a second width greater than the first width.

The piezoelectric wafer formed on the upper surface of the flexible substrate part of the unit ultrasonic probe may have a first height and a third width less than the first width.

Another aspect of the present invention provides an ultrasonic probe module including: a first unit ultrasonic probe which includes a first rear block part, a first flexible substrate part which is stacked on an upper surface of the first rear block part and in which a first wiring pattern is formed, and a first piezoelectric wafer which is stacked on one side of an upper surface of the first flexible substrate part and is in electrical connection with the first flexible substrate part; and a second unit ultrasonic probe which includes a second rear block part which is stacked on the upper surface of the first flexible substrate part, a second flexible substrate part which is stacked on an upper surface of the second rear block part, and a second piezoelectric wafer which is stacked on an upper surface of the second flexible substrate part and is in electrical connection with the second flexible substrate part.

A size of the second rear block part of the ultrasonic probe module may be smaller than that of the first rear block part, the first and second piezoelectric wafers may be formed in the same size, and the first and second piezoelectric wafers may be disposed not to overlap each other.

The first piezoelectric wafer and the second rear block part of the ultrasonic probe module may be formed in the same thickness, and the first piezoelectric wafer and the second rear block part may be spaced apart from each other.

In the ultrasonic probe module, the other ends opposite one ends of the first and second flexible substrate parts on which the first and second piezoelectric wafers are disposed may extend toward outsides of the first and second rear block parts and may be bent from the first and second rear block parts.

A size of the first piezoelectric wafer of the ultrasonic probe module may be smaller than or equal to that of the second piezoelectric wafer.

The second flexible substrate part of the ultrasonic probe module may overlap a part of the first piezoelectric wafer, and the second flexible substrate part may be in electrical connection with the first piezoelectric wafer.

Still another aspect of the present invention provides an ultrasonic probe device including a plurality of ultrasonic probe modules which are formed by stacking at least two unit ultrasonic probes including rear block parts, flexible substrate parts stacked on upper surfaces of the rear block parts, and piezoelectric wafers stacked on one sides of upper surfaces of the flexible substrate parts and in electrical connection with the flexible substrate parts, one ends of the rear block parts formed in each of the ultrasonic probe modules disposed in a staircase shape, the other ends opposite the one ends of the rear block parts aligned at the same position, and the ultrasonic probe modules disposed to face each other.

The one ends of the ultrasonic probe modules of the ultrasonic probe device may be disposed to face each other.

The flexible substrate parts included in each of the ultrasonic probe modules of the ultrasonic probe device may be disposed at outsides of each of the ultrasonic probe modules.

In the ultrasonic probe modules of the ultrasonic probe device, the other ends opposite the one ends of the rear block parts formed in a staircase shape and aligned in the same plane may be disposed to face each other.

The flexible substrate parts of the ultrasonic probe device may be disposed inside the ultrasonic probe modules.

In the ultrasonic probe modules of the ultrasonic probe device, the one end of any one ultrasonic probe module and the other end of the remaining ultrasonic probe module may be disposed to face each other.

The first and second flexible substrate parts of the ultrasonic probe device may extend toward the other sides of the first and second rear block parts and may be bent.

Advantageous Effects

Accordingly, since the ultrasonic probe according to the present invention stacks the unit ultrasonic probes including the piezoelectric wafers to increase the number of channels even though the number of the piezoelectric wafers increases transversally, the ultrasonic probe can prevent a structure of the flexible substrate part from being complicated and prevent the cost from increasing exponentially.

In addition, since the unit probes are stacked in a staggered structure in which the piezoelectric wafers do not overlap each other and formed adjacent to each other, the ultrasonic probe can be easy to manufacture and can be manufactured in a convex or concave structure according to a structure thereof.

MODES OF THE INVENTION

Hereinafter, embodiments of the present invention will be described in detail with reference to the accompanying drawings. In detailed descriptions of the embodiments, technical content which is well-known in the art and has no direct relation to the present invention will be omitted. This serves to convey the principles of the present invention more clearly without unnecessarily obscuring the gist of the present invention by omitting unnecessary descriptions.

Figure 1:
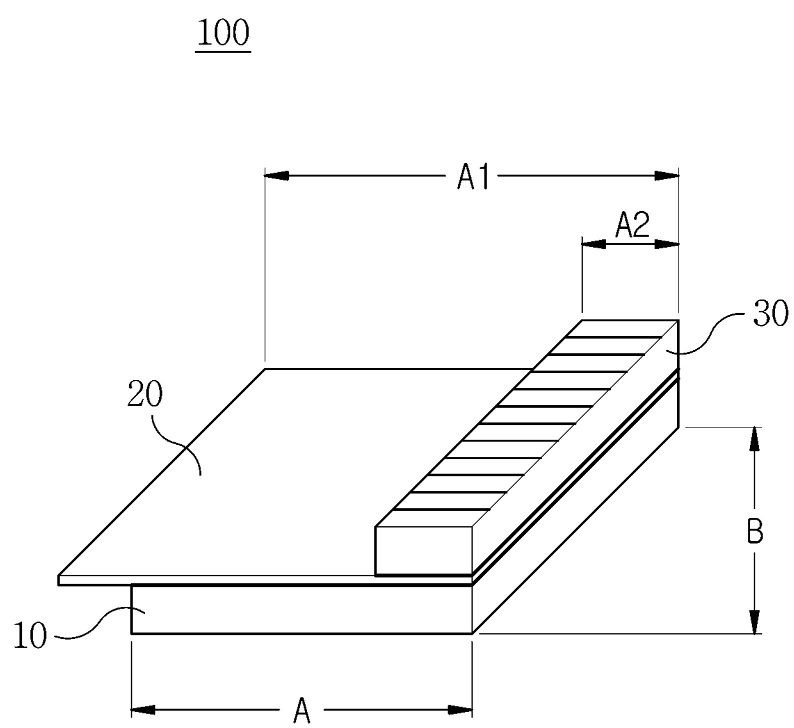
FIG. 1 is a perspective view illustrating a unit ultrasonic probe according to an embodiment of the present invention.
Figure 2:
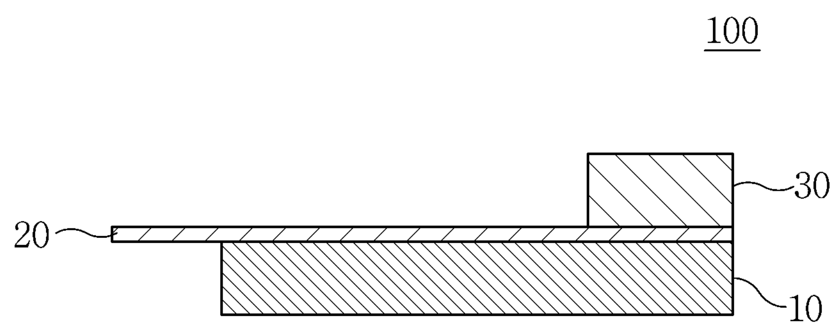
FIG. 2 is a cross-sectional view illustrating the unit ultrasonic probe according to an embodiment of the present invention.

Referring to FIGS. 1 and 2, a unit ultrasonic probe 100 according to an embodiment of the present invention is as follows.

FIGS. 1 and 2 are a cross-sectional view and a perspective view illustrating a unit ultrasonic probe 100 according to an embodiment of the present invention.

The unit ultrasonic probe 100 according to an embodiment of the present invention has a structure in which a rear block part 10, a flexible substrate part 20, a piezoelectric wafer 30 are sequentially stacked.

The rear block part 10 may be positioned at a lowest end of the unit ultrasonic probe 100, absorb an unnecessary ultrasonic signal which proceeds from the piezoelectric wafer 30 toward the rear block part 10, and use a material having a good acoustic absorption characteristic such as a rubber, graphite, and a urethane.

Referring to FIG. 1, the rear block part 10 has a first width A and a first height B.

The flexible substrate part 20 may be stacked on an upper surface of the rear block part 10, wiring patterns may be formed on both surfaces of the flexible substrate part 20, and a flexible printed circuit board (FPCB) may be used for the flexible substrate part 20.

In an embodiment of the present invention, the flexible substrate part 20 has a second width A1 greater than the first width A, and the flexible substrate part 20 has the first height B the same as that of the rear block part 10.

Further, the piezoelectric wafer 30 may be stacked on an upper surface of the flexible substrate part 20, and use a ceramic material such as lead zirconate titanate (PZT), and lead magnesium niobate-lead titanate (PMN-PT) as its material.

The piezoelectric wafer 30 has a third width A2 less than the first width A of the rear block part 10, and the piezoelectric wafer 30 has the first height B the same as that of the rear block part 10.

In an embodiment of the present invention, referring to FIGS. 1 and 2, one end of the rear block part 10, one end of the flexible substrate part 20, and one end of the piezoelectric wafer 30 are aligned and disposed on the same plane, the other end opposite the one end the rear block part 10, the other end opposite the one end of the flexible substrate part 20, and the other end opposite the one end of the piezoelectric wafer 30 are disposed at different positions.

Figure 3:
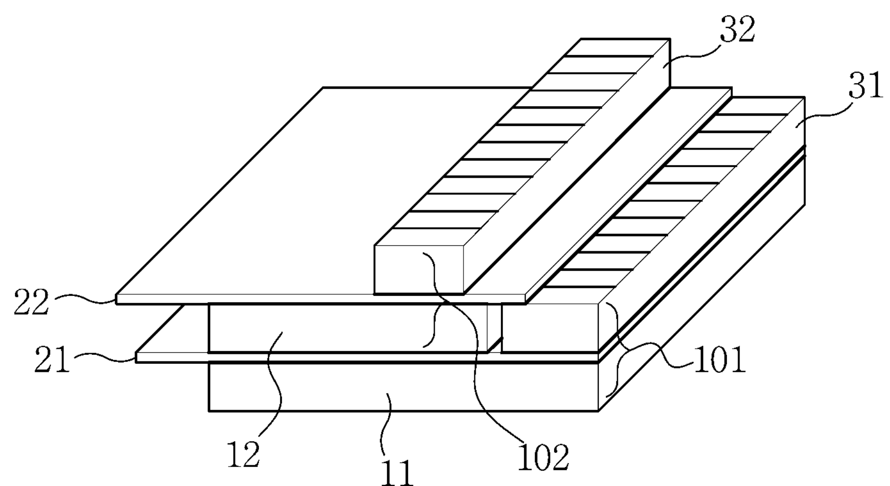
FIG. 3 is a perspective view illustrating an ultrasonic probe module according to an embodiment of the present invention.
Figure 4:
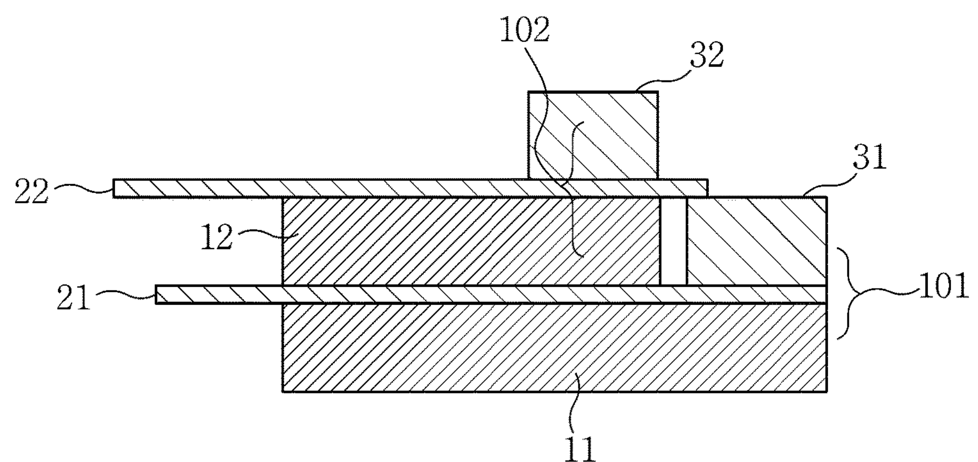
FIG. 4 is a cross-sectional view illustrating the ultrasonic probe module according to an embodiment of the present invention.

Referring to FIGS. 3 and 4, an ultrasonic probe module 200 according to an embodiment of the present invention is as follows.

FIGS. 3 and 4 are a cross-sectional view and a perspective view illustrating an ultrasonic probe module 200 according to an embodiment of the present invention.

Referring to FIGS. 3 and 4, an ultrasonic probe module 200 includes a first unit ultrasonic probe 101 and a second unit ultrasonic probe 102.

The first unit ultrasonic probe 101 includes a first rear block part 11, a first flexible substrate part 21, and a first piezoelectric wafer 31.

The first flexible substrate part 21 is stacked on an upper surface of the first rear block part 11, and the first piezoelectric wafer 31 is stacked on one side of an upper surface of the first flexible substrate part 21 and is in electrical connection with the first flexible substrate part 21.

The second unit ultrasonic probe 102 is stacked on an upper surface of the first unit ultrasonic probe 101, and the second unit ultrasonic probe 102 includes a second rear block part 12, a second flexible substrate part 22, and a second piezoelectric wafer 32.

The second rear block part 12 is stacked on the upper surface of the first flexible substrate part 21 and is spaced apart from the first piezoelectric wafer 31.

The second flexible substrate part 22 is stacked on an upper surface of the second rear block part 12, and in addition, is stacked on a partial surface of the first piezoelectric wafer 31, and the second flexible substrate part 22 is in electrical connection with the first piezoelectric wafer 31.

The second piezoelectric wafer 32 is stacked on an upper surface of the second flexible substrate part 22 in an area of the second rear block part 12 and in electrical connection with the second flexible substrate part 22.

Accordingly, the ultrasonic probe module 200 has a structure in which the first unit ultrasonic probe 101 and the second unit ultrasonic probe 102 are sequentially stacked, and here, the number of the unit ultrasonic probes is not limited thereto.

Particularly, the first rear block part 11 has a size including the first piezoelectric wafer 31 positioned on the upper surface thereof to absorb an ultrasonic wave radiated toward a rear surface of the first piezoelectric wafer 31.

In addition, the second rear block part 12 has a size including the second piezoelectric wafer 32 positioned on the upper surface thereof to absorb an ultrasonic wave radiated toward a rear surface of the second piezoelectric wafer 32, and has the same thickness as the first piezoelectric wafer 31 so that the second flexible substrate part 22 stacked on the upper surfaces of the second rear block part 12 and the first piezoelectric wafer 31 is parallel to the first flexible substrate part 21.

In order to prevent the first flexible substrate part 21 and the second flexible substrate part 22 from entirely covering front surfaces of the first piezoelectric wafer 31 and the second piezoelectric wafer 32, the first and second flexible substrate parts 21 and 22 extend in a direction opposite to the side in which the first piezoelectric wafer 31 and the second piezoelectric wafer 32 are positioned, and the first and second flexible substrate parts 21 and 22 protrude to outsides of the first and second rear block parts 11 and 12 as illustrated in FIGS. 3 and 4.

In an embodiment of the present invention, as illustrated in FIGS. 3 and 4, a size of the second rear block part 12 is formed smaller than that of the first rear block part 11.

One ends of the first and second rear block parts 11 and 12 having different sizes are aligned and disposed on the same plane, and accordingly, the other ends opposite the one ends of the first and second rear block parts 11 and 12 are disposed in the staircase shape as illustrated in FIGS. 3 and 4.

In addition, the second piezoelectric wafer 32 is stacked on the upper surface of the second flexible substrate part 22 in the area of the second rear block part 12, and the second piezoelectric wafer 32 is disposed not to overlap the first piezoelectric wafer 31.

So that the first and second piezoelectric wafers 31 and 32 are disposed not to overlap each other, the first piezoelectric wafer 31 and the second rear block part 12 are disposed spaced apart as illustrated in FIG. 4, and the first piezoelectric wafer 31 and the second rear block part 12 are formed in the same thickness.

In an embodiment of the present invention, since the first and second piezoelectric wafers 31 and 32 are formed in the same size, and the ends of the first and second rear block parts 11 and 12 are disposed in the staircase shape, the first and second piezoelectric wafers 31 and 32 are also disposed in the staircase shape as illustrated in FIGS. 3 and 4.

Figure 5:
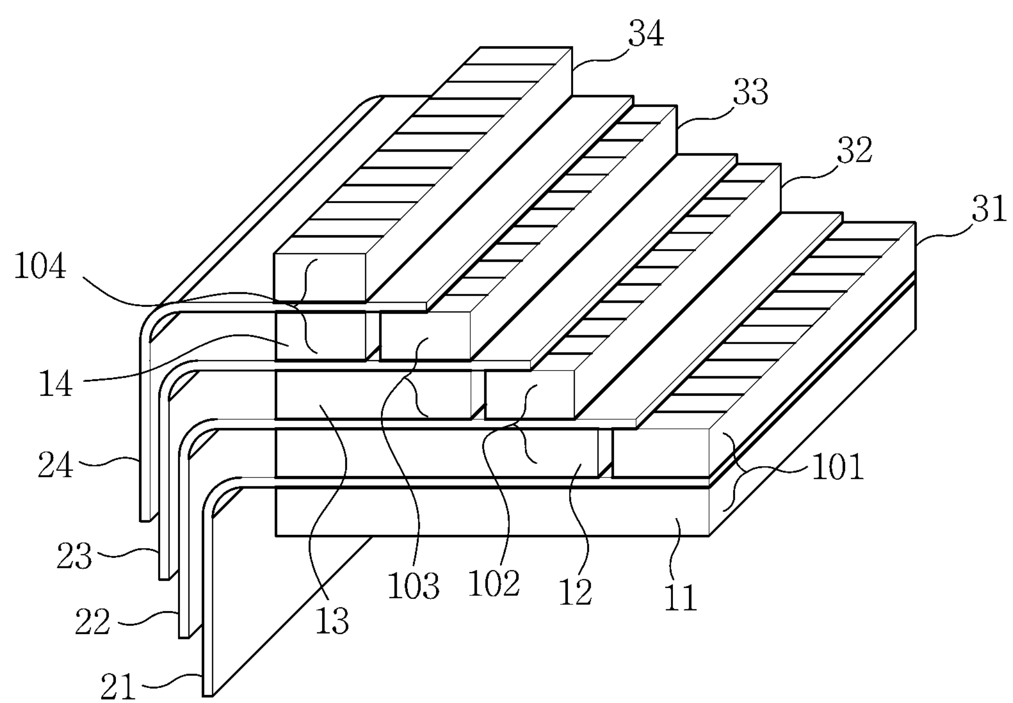
FIG. 5 is a perspective view illustrating a stacked structure of the unit ultrasonic probes according to an embodiment of the present invention.

A shape in which four unit ultrasonic probes 101, 102, 103, and 104 are stacked according to an embodiment of the present invention is illustrated in FIG. 5, and an ultrasonic probe module in which the four unit ultrasonic probes are assembled is illustrated in FIG. 5.

FIG. 5 is a perspective view illustrating a shape in which unit ultrasonic probes 101, 102, 103, and 104 forming an ultrasonic probe module are sequentially stacked, and in order to prevent piezoelectric wafers 31, 32, 33, and 34 from overlapping each other, the piezoelectric wafers 31, 32, 33, and 34 are stacked in the staircase shape. Here, the number of the stacked unit ultrasonic probes is not limited thereto.

Rear block parts 11, 12, 13, and 14 serve to support the piezoelectric wafers 31, 32, 33, and 34, and in order to prevent the piezoelectric wafers 31, 32, 33, and 34 from overlapping each other, sizes of the rear block parts 11, 12, 13, and 14 decrease toward the top.

The rear block parts 11, 12, 13, and 14 have shapes in which sizes thereof decrease toward the top, and when either of ends of the rear block parts 11, 12, 13, and 14 are aligned and positioned on the same plane, one ends of the rear block parts 11, 12, 13, and 14 are disposed in the staircase shape and the other ends opposite to the one ends are aligned on the same plane.

In addition, the piezoelectric wafers 31, 32, 33, and 34 are respectively positioned parallel to each other at the one ends of upper surfaces of the rear block parts 11, 12, 13, and 14, and accordingly, the piezoelectric wafers 31, 32, 33, and 34 are disposed not to overlap each other.

Flexible substrate parts 21, 22, 23, and 24 are in electrical connection with the piezoelectric wafers 31, 32, 33, and 34, respectively.

In an embodiment of the present invention, the flexible substrate parts 21, 22, 23, and 24 are bent upward or downward from outsides of the rear block parts 11, 12, 13, and 14 as illustrated in FIG. 5.

Hereinafter, referring to FIG. 6, an ultrasonic probe device 301 using the ultrasonic probe modules illustrated in FIG. 5 is as follows.

In an embodiment of the present invention, the ultrasonic probe device 301 is formed by combining ultrasonic probe modules 301*a* and 301*b* illustrated in FIG. 5.

Figure 6:
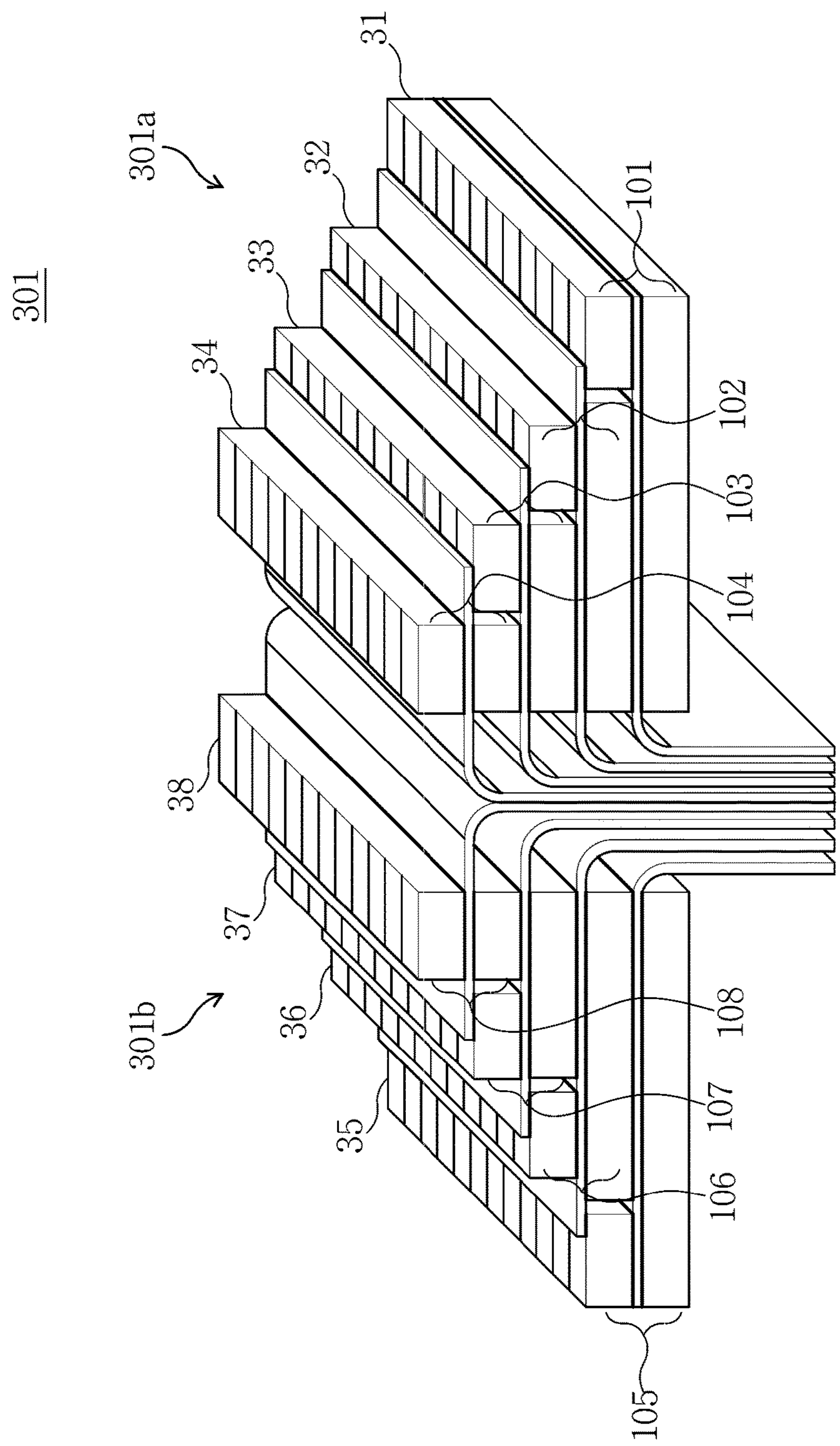
FIG. 6 is a perspective view illustrating an ultrasonic probe device in which the probe modules according to an embodiment of the present invention are arrayed.

FIG. 6 is a perspective view illustrating an ultrasonic probe device including at least two ultrasonic probe modules 301*a* and 301*b* including unit ultrasonic probes 101, 102, 103, 104, 105, 106, 107, and 108 according to an embodiment of the present invention.

In FIG. 6, one sides of rear blocks which are included in an ultrasonic probe module 301*a* and stacked in different sizes, and one sides of rear blocks which are included in the remaining ultrasonic probe module 301*b* stacked in different sizes are disposed in the staircase shape, and the other sides opposite the one sides of the rear blocks are respectively aligned on the same plane.

The ultrasonic probe modules 301*a* and 301*b* illustrated in FIG. 6 are disposed to face each other, and in each of the ultrasonic probe modules 301*a* and 301*b* illustrated in FIG. 6, the other sides of the rear blocks, which are aligned on the same plane, are disposed to face each other.

Further, separation distances between the piezoelectric wafers 31, 32, 33, 34, 35, 36, 37, and 38 which symmetrically face each other with respect to a direction in which lengths of the flexible substrate parts increase when the piezoelectric wafers 31, 32, 33, 34, 35, 36, 37, and 38 are stacked upward gradually decrease to form a convex structure, and here, the flexible substrate parts included in the pair of ultrasonic probe modules 301*a* and 301*b* extend toward the space between the pair of ultrasonic probe modules 301*a* and 301*b* and are bent.

In addition, the convex structure may be horizontally arrayed and form an ultrasonic probe, and here, the number of the convex structures is not limited thereto.

Figure 7:
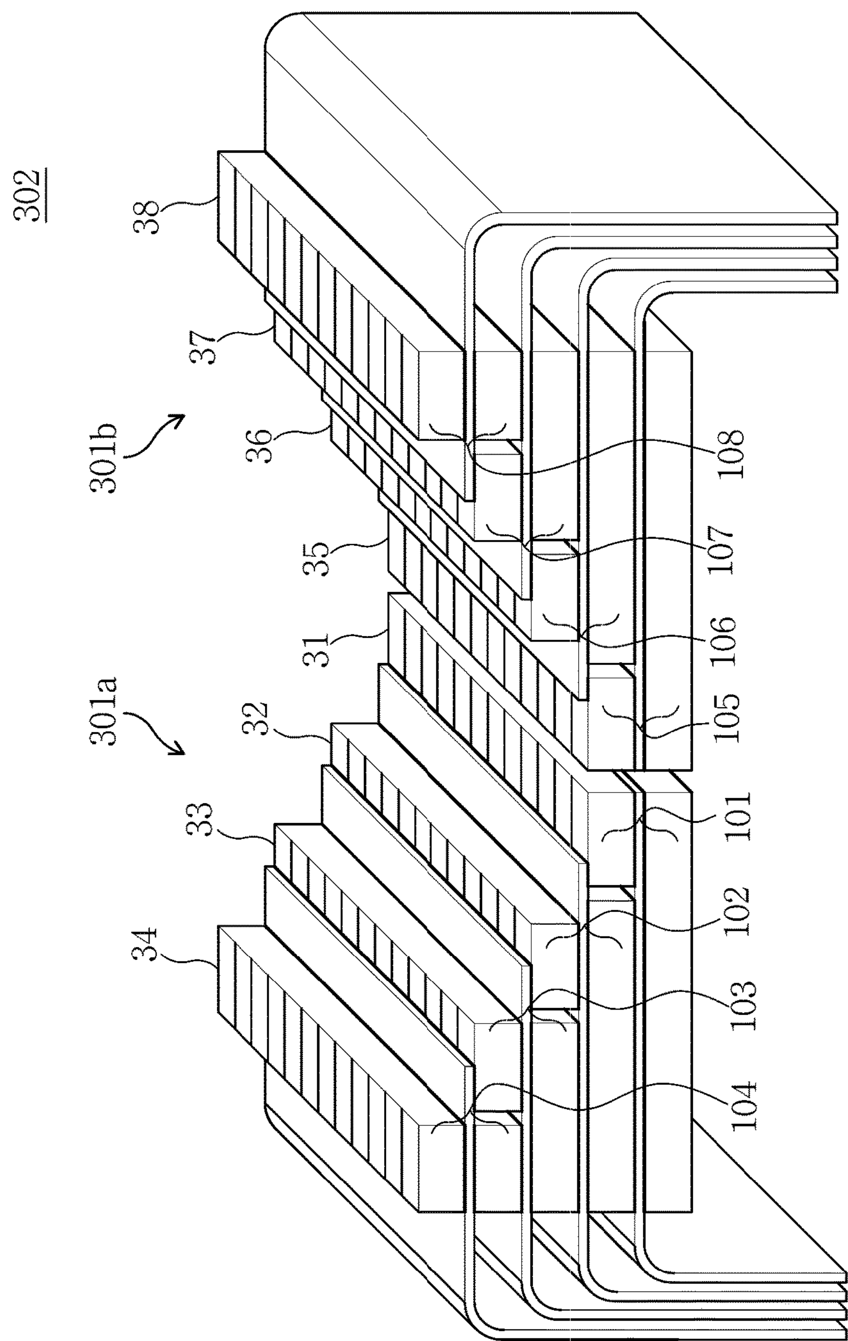
FIG. 7 is another perspective view illustrating an ultrasonic probe device in which the probe modules according to an embodiment of the present invention are arrayed.

Referring to FIG. 7, an ultrasonic probe device 302 according to an embodiment of the present invention is as follows.

In an embodiment of the present invention, an ultrasonic probe device 302 is formed by combining the ultrasonic probe modules 301*a* and 301*b* illustrated in FIG. 7, and the ultrasonic probe modules 301*a* and 301*b* include the unit ultrasonic probes 101, 102, 103, 104, 105, 106, 107, and 108 disposed in symmetric shapes.

In FIG. 7, one sides of rear blocks included in the ultrasonic probe module 301*a* and stacked in different sizes, and one sides of rear blocks included in the remaining ultrasonic probe module 301*b* and stacked in different sizes are disposed in the staircase shape, and the other sides opposite the one sides of the rear blocks are aligned on the same plane.

The ultrasonic probe modules 301*a* and 301*b* illustrated in FIG. 7 are disposed to face each other, and in the ultrasonic probe modules 301*a* and 301*b* illustrated in FIG. 7, the one sides of the rear blocks, which are disposed in the staircase shape, are disposed to face each other.

The piezoelectric wafers 31, 32, 33, 34, 35, 36, 37, and 38 are positioned adjacent to each other in a direction in which lengths of the flexible substrate parts increase when the piezoelectric wafers 31, 32, 33, 34, 35, 36, 37, and 38 are stacked upward, to prevent overlapping thereof.

Further, separation distances between the piezoelectric wafers 31, 32, 33, 34, 35, 36, 37, and 38 which symmetrically face each other with respect to a direction in which the lengths of the flexible substrate parts increase when the piezoelectric wafers 31, 32, 33, 34, 35, 36, 37, and 38 are stacked upward increase to form a concave structure, and the flexible substrate parts extend toward outsides of the pair of ultrasonic probe modules 301*a* and 301*b* and are bent.

The ultrasonic probe modules 301*a* and 301*b* may be horizontally arrayed in the concave structure to form an ultrasonic probe, and here, the number of the concave structures horizontally arrayed is not limited thereto.

Figure 8:
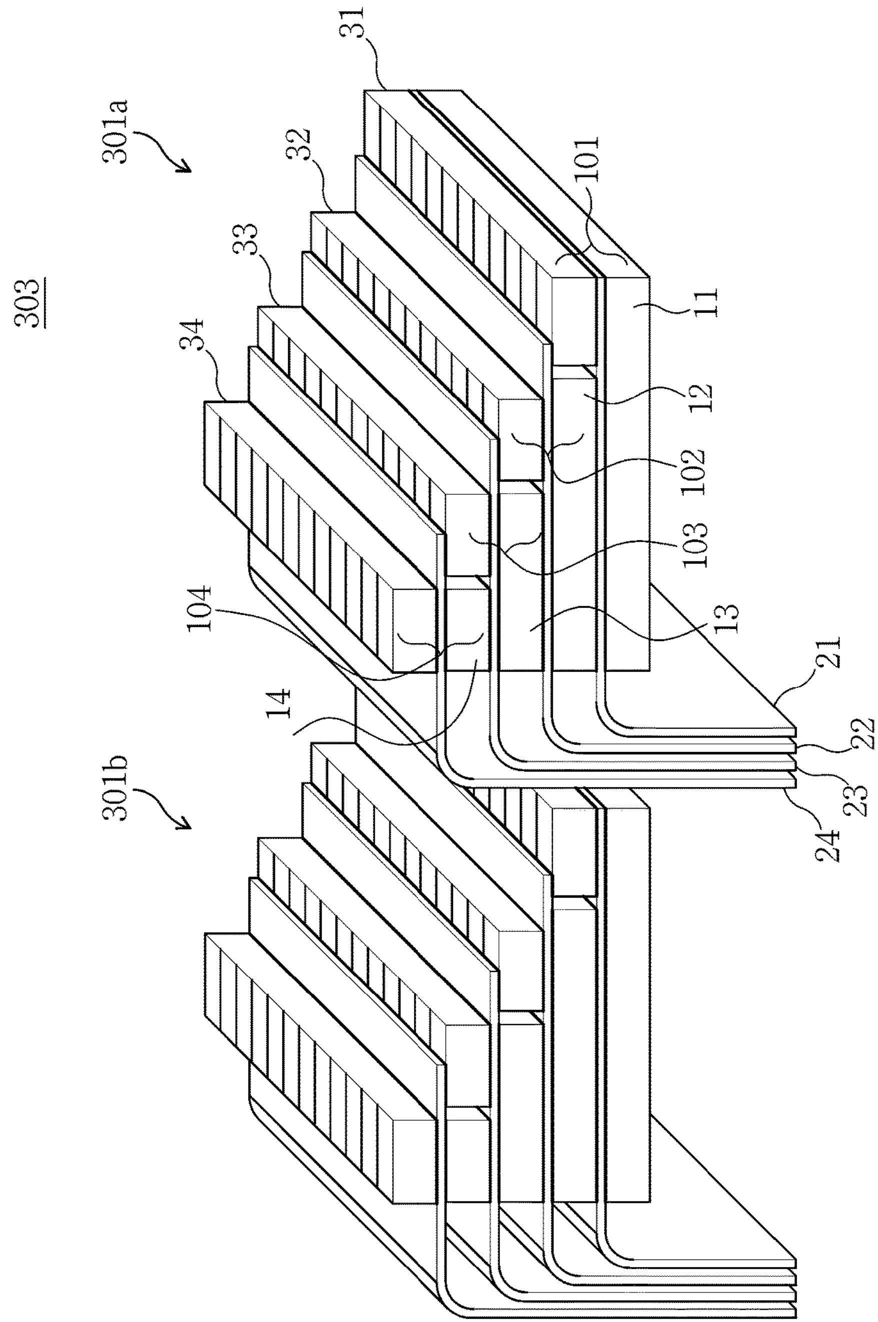
FIG. 8 is still another perspective view illustrating an ultrasonic probe device in which the probe modules according to an embodiment of the present invention are arrayed.

Referring to FIG. 8, an ultrasonic probe device 303 according to an embodiment of the present invention is as follows. FIG. 8 is a perspective view illustrating an ultrasonic probe device 303 including the ultrasonic probe modules 301*a* and 301*b* in which the four unit ultrasonic probes 101, 102, 103, and 104 according to an embodiment of the present invention are stacked.

In an embodiment of the present invention, the ultrasonic probe device 303 is formed by combining the ultrasonic probe modules 301*a* and 301*b* illustrated in FIG. 8, and each of the ultrasonic probe modules 301*a* and 301*b* includes the unit ultrasonic probes 101, 102, 103, and 104 disposed in symmetrical shapes.

In FIG. 8, one sides of the rear blocks included in the ultrasonic probe module 301*a* and stacked in different sizes, and one sides of the rear blocks included in the remaining ultrasonic probe module 301*b* and stacked in different sizes are disposed in the staircase shape, and the other sides opposite the one sides of the rear blocks are arrayed on the same plane.

The ultrasonic probe modules 301*a* and 301*b* illustrated in FIG. 8 are disposed to face each other, and in the ultrasonic probe modules 301*a* and 301*b* illustrated in FIG. 8, the one sides of the rear blocks disposed in the staircase shape and the other sides of the rear blocks disposed on the same plane are disposed to face each other.

The piezoelectric wafers are positioned adjacent to each other in an opposite side of the direction in which lengths of the flexible substrate parts increase when the piezoelectric wafers are stacked, to prevent overlapping thereof.

Figure 9:
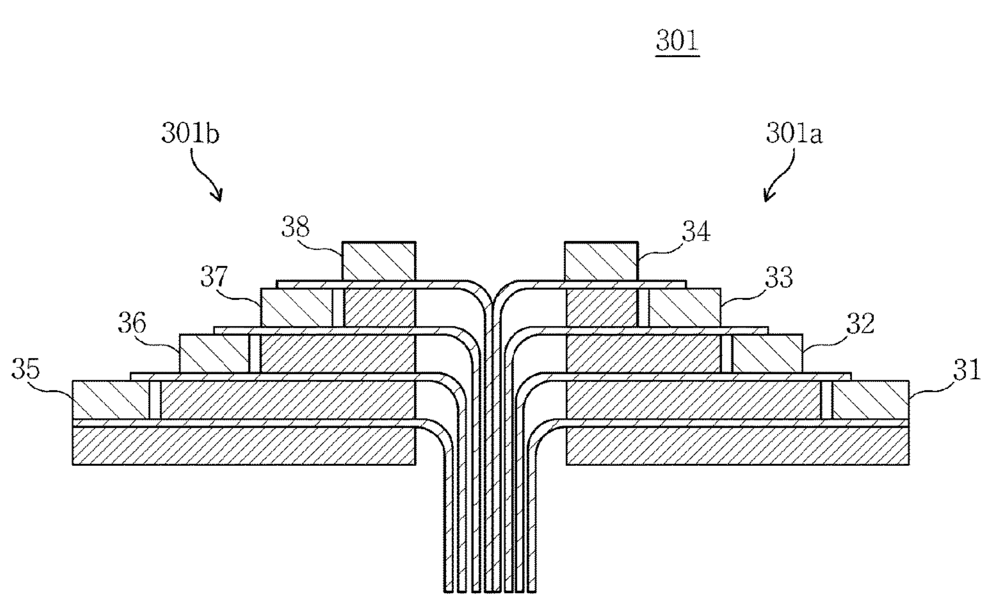
FIG. 9 is a cross-sectional view illustrating the ultrasonic probe device of FIG. 6.

FIG. 9 is a cross-sectional view illustrating the ultrasonic probe device 301 having a structure in which the ultrasonic probe modules 301*a* and 301*b* including the unit ultrasonic probes 101, 102, 103, 104, 105, 106, 107, and 108 according to an embodiment of the present invention illustrated in FIG. 6 symmetrically face each other with respect to the direction in which the lengths of the flexible substrate parts extend.

Figure 10:
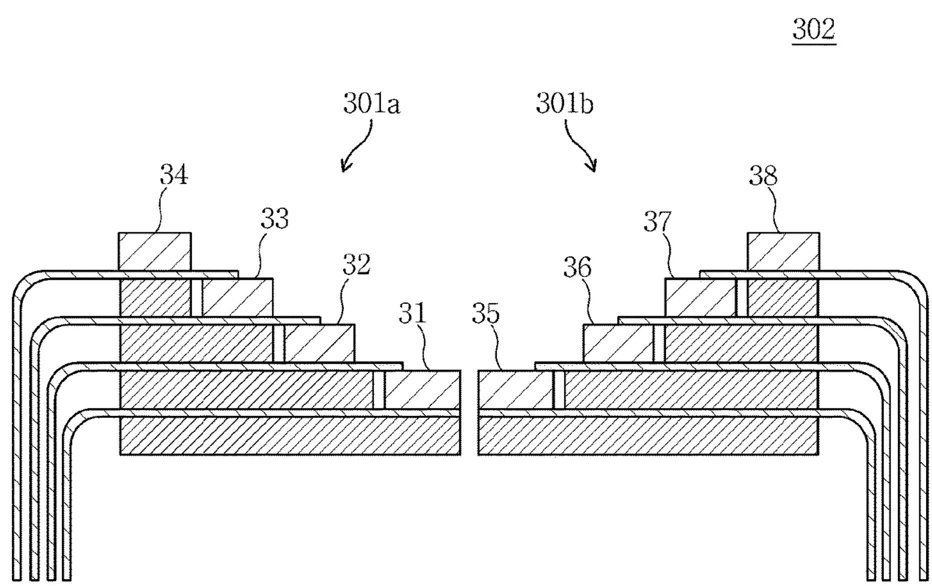
FIG. 10 is a cross-sectional view illustrating the ultrasonic probe device of FIG. 7.

FIG. 10 is a cross-sectional view illustrating the ultrasonic probe device 302 having a structure in which the ultrasonic probe modules 301*a* and 301*b* including the unit ultrasonic probes 101, 102, 103, 104, 105, 106, 107, and 108 according to an embodiment of the present invention illustrated in FIG. 7 symmetrically face each other with respect to the opposite side of the direction in which the lengths of the flexible substrate parts extend.

Figure 11:
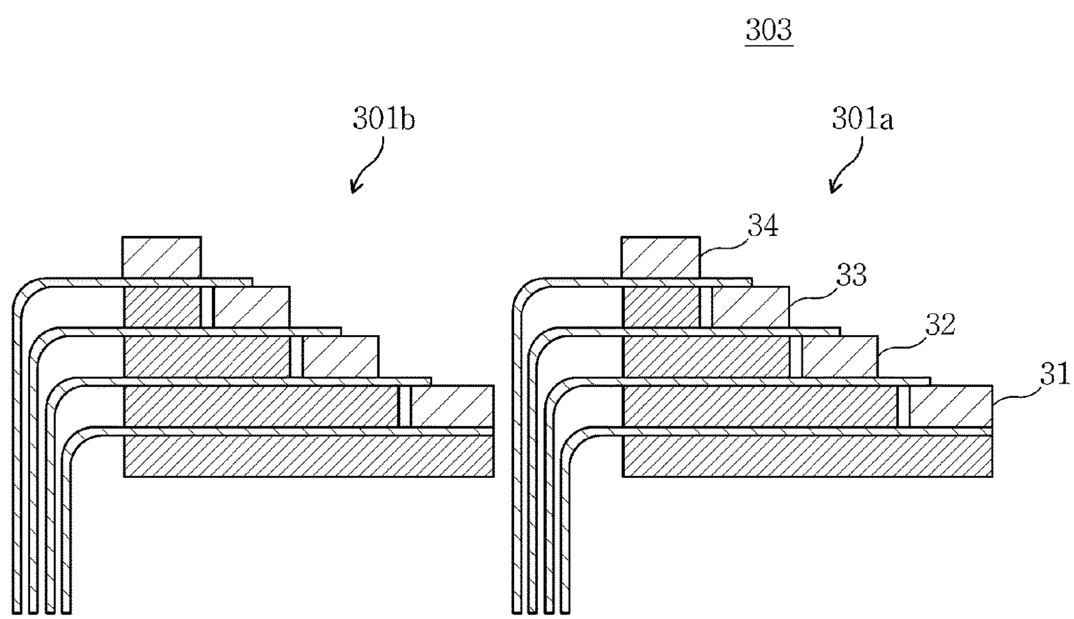
FIG. 11 is a cross-sectional view illustrating the ultrasonic probe device of FIG. 8.

FIG. 11 is a cross-sectional view illustrating the ultrasonic probe device 303 having a structure in which the stacked ultrasonic probe modules 301*a* and 301*b* including the unit ultrasonic probes 101, 102, 103, and 104 according to an embodiment of the present invention illustrated in FIG. 8 have a horizontally arrayed shape.

Figure 12:
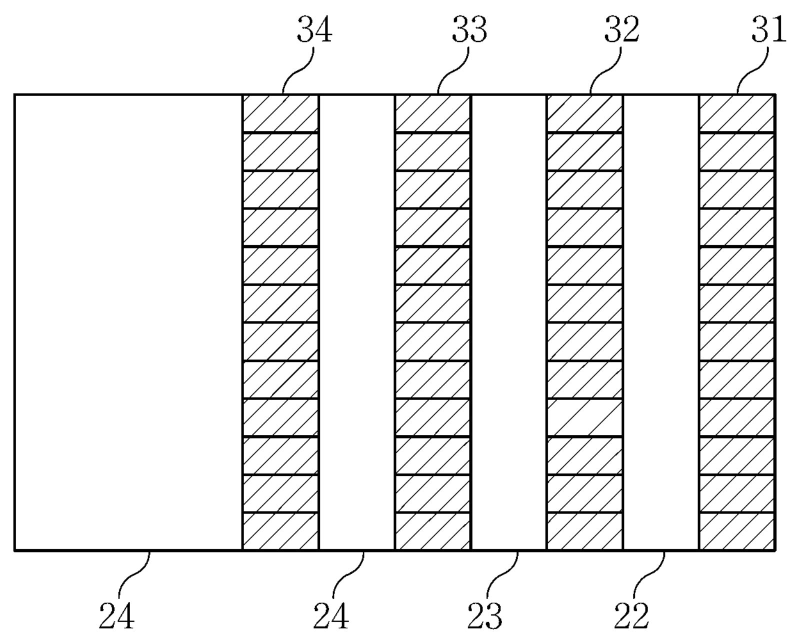
FIG. 12 is a view illustrating a shape, in which the unit ultrasonic probes including piezoelectric wafers having the same size are stacked according to an embodiment of the present invention, as seen from above.

Referring to FIG. 12, a shape of the stacked unit ultrasonic probes 101, 102, 103, and 104 according to an embodiment of the present invention is as follows. FIG. 12 is a view illustrating a shape in which the unit ultrasonic probes 101, 102, 103, and 104 according to an embodiment of the present invention are stacked, as seen from above, and a view illustrating that areas of piezoelectric wafers 31, 32, 33, and 34 of the unit ultrasonic probes 101, 102, 103, and 104 are the same.

Figure 13:
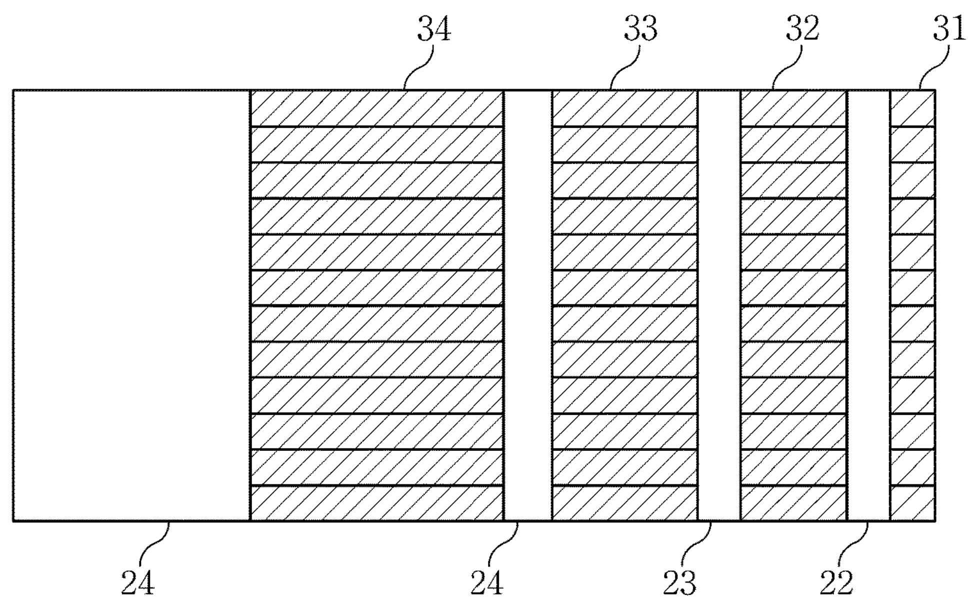
FIG. 13 is a view illustrating a shape, in which the unit ultrasonic probes including piezoelectric wafers having different sizes are stacked according to an embodiment of the present invention, as seen from above.

Referring to FIG. 13, a stacked shape of the unit ultrasonic probes 101, 102, 103, 104 according to an embodiment of the present invention is as follows. FIG. 13 is a view illustrating a stacked shape of the unit ultrasonic probes 101, 102, 103, and 104 according to an embodiment of the present invention as seen from above, and a view illustrating that areas of the piezoelectric wafers 31, 32, 33, and 34 of the unit ultrasonic probes 101, 102, 103, and 104 increase in a direction in which the length of the flexible substrate part 24 extends.

Figure 14:
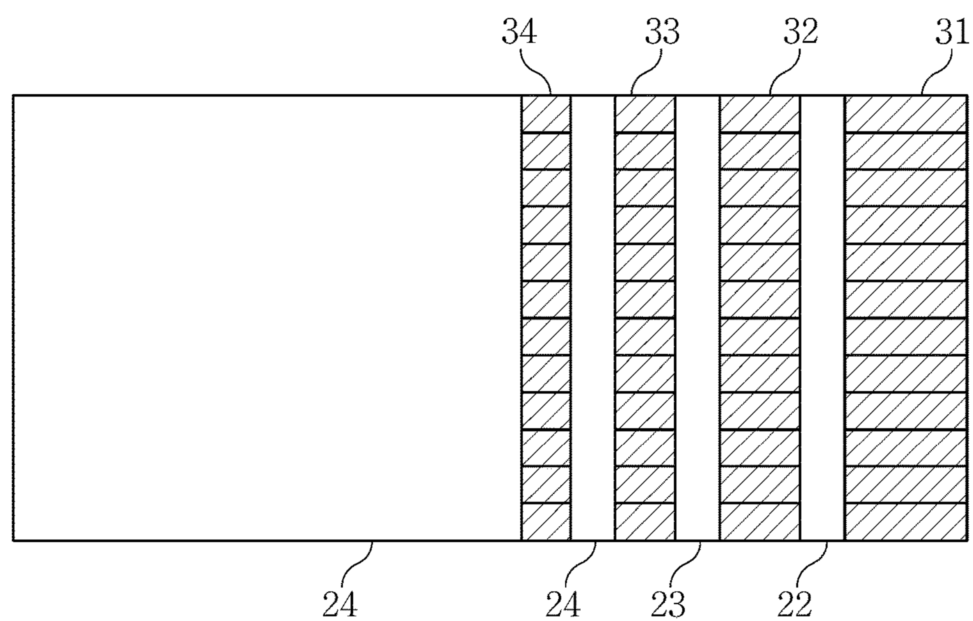
FIG. 14 is another view illustrating a shape, in which the unit ultrasonic probes including piezoelectric wafers having different sizes are stacked according to an embodiment of the present invention, as seen from above.

Referring to FIG. 14, a stacked shape of the unit ultrasonic probes 101, 102, 103, and 104 according to an embodiment of the present invention is as follows. FIG. 14 is a view illustrating a stacked shape of unit ultrasonic probes 101, 102, 103, and 104 according to an embodiment of the present invention as seen from above, and is a view that areas of the piezoelectric wafers 31, 32, 33, and 34 of the unit ultrasonic probes 101, 102, 103, and 104 decrease in a direction in which the length of the flexible substrate part 24 extends.

Figure 15:
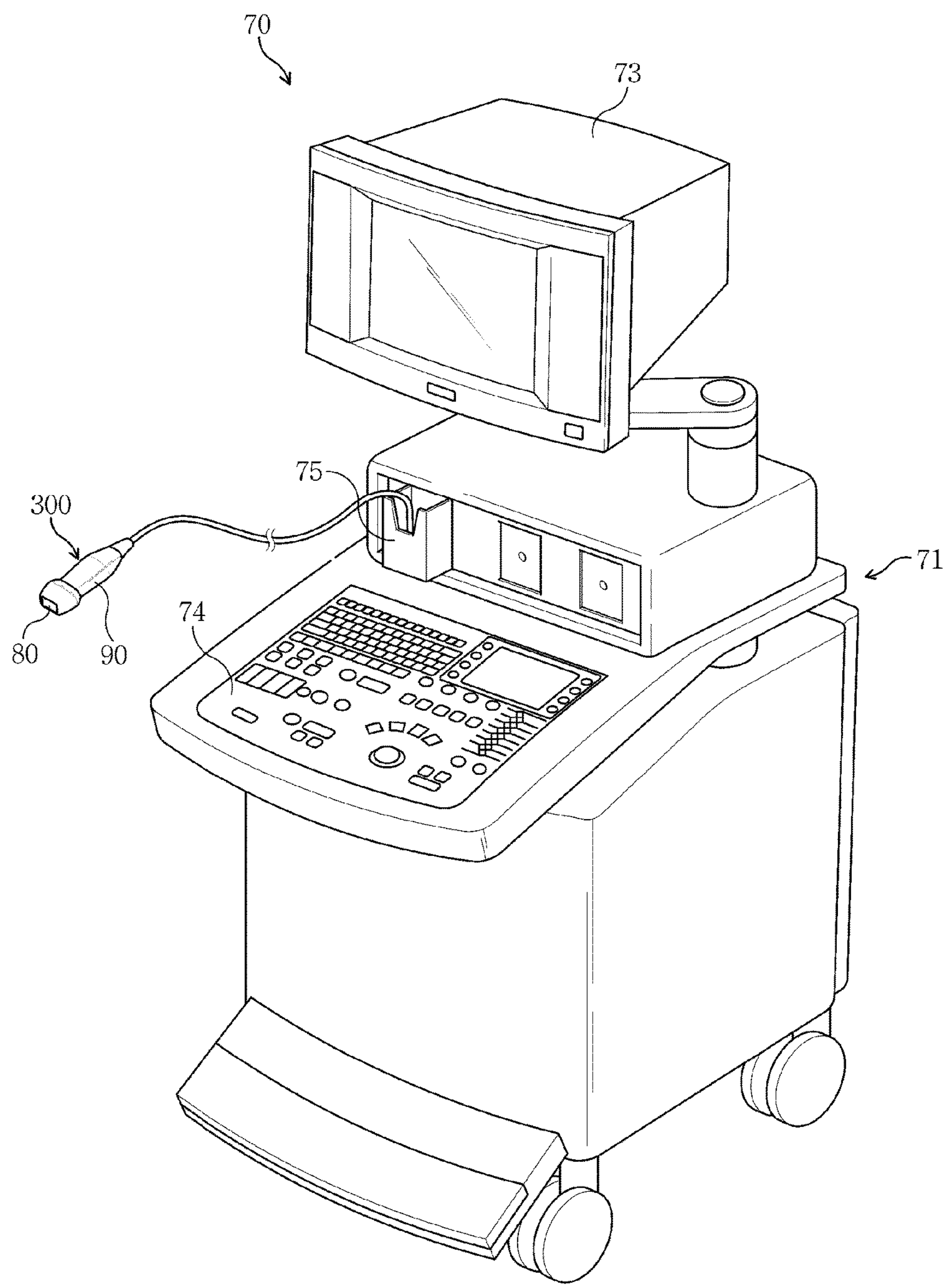
FIG. 15 is a view illustrating an ultrasonic image device according to an embodiment of the present invention.

Referring to FIG. 15, an ultrasonic imaging device 70 according to an embodiment of the present invention is as follows. An ultrasonic image device 70 seen in FIG. 15 includes a main body 71, an ultrasonic probe 300, a display 73, an input part 74, and a connector 75.

The ultrasonic probe 300 includes an acoustic lens 80 which contacts a diseased area of a patient and a case 90 which surrounds the remaining parts which form the ultrasonic probe 300. The acoustic lens 80 may be a lens which is used for focusing of an ultrasonic image and use silicon as its material. Meanwhile, the remaining parts inside the case 90 ware described above in detail.

As described above, the ultrasonic probe module, the ultrasonic probe and the manufacturing method thereof according to the present invention are described with reference to the accompanying embodiments. Meanwhile, the embodiments disclosed in this specification and drawings are only examples to help understanding of the invention and the invention is not limited thereto. It is apparent to those skilled in the art that various modifications based on the technological scope of the invention in addition to the embodiments disclosed herein can be made.

INDUSTRIAL APPLICABILITY

The provided above can be used for medical ultrasonic examination devices which examine abnormal tissues, or identify the presence of the abnormal tissues using images generated through signals which are reflected ultrasonic waves radiated to diseased areas, and which are mainly used for examining lesion tissues such as tumors or in prenatal diagnosis, using ultrasonic waves, and can also be applied to examination devices which generate ultrasonic waves and perform nondestructive inspections and the like.

The invention claimed is:

1. An ultrasonic probe module comprising:

a first unit ultrasonic probe having a first flexible substrate forming a first wiring pattern, a first piezoelectric wafer disposed on one side of an upper surface of the first flexible substrate, and electrically connected with the first flexible substrate, and a first block disposed on a lower surface of the first flexible substrate; and a second unit ultrasonic probe having a second flexible substrate forming a second wiring pattern, a second piezoelectric wafer disposed on an upper surface of the second flexible substrate, and electrically connected with the second flexible substrate, and a second block disposed on a lower surface of the second flexible substrate and stacked on other side of the first flexible substrate, wherein the first piezoelectric wafer and the second block are formed in the same thickness, and wherein the second block and the first piezoelectric wafer are spaced apart from each other between the first and second flexible substrates.

2. The ultrasonic probe module of claim 1, wherein a size of the second block is smaller than that of the first block, the first and second piezoelectric wafers are formed in the same size, and the first and second piezoelectric wafers are disposed on the first and second flexible substrate, respectively, without overlap each other.

3. The ultrasonic probe module of claim 1, wherein one ends of the first and second flexible substrates extend beyond the first and second block, respectively, and are bent.

4. The ultrasonic probe module of claim 1, wherein a size of the first piezoelectric wafer is bigger than or equal to a size of the second piezoelectric wafer.

5. The ultrasonic probe module of claim 1, wherein the second flexible substrate overlaps a part of the first piezoelectric wafer, and the second flexible substrate is in electrical connection with the first piezoelectric wafer.

6. An ultrasonic probe device comprising:

a first plurality of ultrasonic probes formed by stacking from a lowest ultrasonic probe among the first plurality of ultrasonic probes, each ultrasonic probe of the first plurality of ultrasonic probes comprising:

a first flexible substrate having a wiring pattern thereon, a first piezoelectric wafer disposed on one side of an upper surface of the first flexible substrate, and electrically connected with the first flexible substrate, and a first block disposed on a lower surface of the first flexible substrate, wherein each first block of the first plurality of ultrasonic probes is stacked on an upper surface of a lower first flexible substrate of a lower ultrasonic probe disposed under the each block, except a first block of the lowest ultrasonic probe among the first plurality of ultrasonic probes; and a second plurality of ultrasonic probes formed by stacking from a lowest ultrasonic probe among the second plurality of ultrasonic probes, each ultrasonic probe of the second plurality of ultrasonic probes comprising:

a second flexible substrate having a wiring pattern thereon, a second piezoelectric wafer disposed on one side of an upper surface of the second flexible substrate and electrically connected with the second flexible substrate, and a second block disposed on a lower surface of the second flexible substrate, wherein each second block of the second plurality of ultrasonic probes is stacked on an upper surface of an adjacent second flexible substrate of an adjacent ultrasonic probe disposed under the each second block, except a second block of the lowest ultrasonic probe among the second plurality of ultrasonic probes, wherein one end of stacked first blocks of the first plurality of ultrasonic probes is formed in a staircase shape and other end, opposite the one end, of the stacked first blocks are aligned, wherein one end of stacked second blocks of the second plurality of ultrasonic probes is formed in a staircase shape and other end, opposite the one end, of the stacked second blocks are aligned, and wherein the first and second plurality of ultrasonic probes are disposed side by side each other.

7. The ultrasonic probe device of claim 6, wherein the one ends of the stacked first and second blocks of the first and second plurality of ultrasonic probes are disposed to face each other so that the first and second plurality of ultrasonic probes are disposed in symmetry.

8. The ultrasonic probe device of claim 6, wherein the other ends of the stacked first and second blocks of the first and second plurality of ultrasonic probes are disposed to face each other so that the first and second plurality of ultrasonic probes are disposed in symmetry.

9. The ultrasonic probe device of claim 6, wherein the one end of the stacked first blocks of the first plurality of ultrasonic probes and the other end of the stacked second blocks of the second plurality of ultrasonic probes are disposed to face each other.

10. The ultrasonic probe device of claim 6, wherein the first flexible substrate of the each ultrasonic probe of the first plurality of ultrasonic probes extends beyond the other end of the stacked first blocks of the first plurality of ultrasonic probes and is bent.

* * * * *